(12) United States Patent
Sato

(10) Patent No.: US 11,925,313 B2
(45) Date of Patent: Mar. 12, 2024

(54) ENDOSCOPE AND ENDOSCOPE SYSTEM

(71) Applicant: OLYMPUS CORPORATION, Tokyo (JP)

(72) Inventor: Eijiro Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 805 days.

(21) Appl. No.: 17/021,473

(22) Filed: Sep. 15, 2020

(65) Prior Publication Data

US 2021/0068616 A1 Mar. 11, 2021

Related U.S. Application Data

(63) Continuation of application No. PCT/JP2018/029834, filed on Aug. 8, 2018.

(30) Foreign Application Priority Data

Mar. 16, 2018 (JP) .................................. 2018-049127

(51) Int. Cl.
*A61B 1/00* (2006.01)

(52) U.S. Cl.
CPC ........ *A61B 1/0008* (2013.01); *A61B 1/00135* (2013.01)

(58) Field of Classification Search
CPC ............ A61B 1/0008; A61B 1/000135; A61B 1/00087; A61B 1/00089; A61B 1/00098; A61B 1/00101; A61B 1/00073
See application file for complete search history.

(56) References Cited

U.S. PATENT DOCUMENTS

| | | | | | |
|---|---|---|---|---|---|
| 4,616,631 | A | * | 10/1986 | Takahashi | A61B 1/00165 600/920 |
| 4,826,280 | A | * | 5/1989 | Hiramoto | A61B 1/00073 385/116 |
| 5,489,256 | A | * | 2/1996 | Adair | A61B 1/00101 600/156 |
| 5,630,795 | A | * | 5/1997 | Kuramoto | A61B 1/00137 604/35 |
| 5,725,477 | A | * | 3/1998 | Yasui | A61B 1/00091 600/125 |
| 6,071,233 | A | * | 6/2000 | Ishikawa | A61B 1/0014 600/129 |

(Continued)

FOREIGN PATENT DOCUMENTS

| | | |
|---|---|---|
| JP | 11-192203 A | 7/1999 |
| JP | 2002-200034 A | 7/2002 |

(Continued)

OTHER PUBLICATIONS

International Search Report dated Oct. 16, 2018 received in PCT/JP2018/029834.

*Primary Examiner* — Timothy J Neal
(74) *Attorney, Agent, or Firm* — Scully, Scott, Murphy & Presser, P.C.

(57) ABSTRACT

An endoscope includes: an insertion portion configured to be inserted into a subject; and a channel fixing portion disposed on an outer periphery of the insertion portion and configured such that a part or all of a long channel tube is fixed in a state of being embedded in a distal end portion of the insertion portion.

20 Claims, 11 Drawing Sheets

(56) References Cited

U.S. PATENT DOCUMENTS

| | | | |
|---|---|---|---|
| 2004/0210111 A1* | 10/2004 | Okada | A61B 1/00087 600/106 |
| 2004/0230096 A1* | 11/2004 | Stefanchik | A61B 1/00073 600/128 |
| 2005/0085694 A1* | 4/2005 | Nakao | A61B 1/00073 600/128 |
| 2006/0270905 A1* | 11/2006 | Monga | A61B 1/307 600/153 |
| 2007/0073320 A1 | 3/2007 | Mikkaichi et al. | |
| 2007/0106113 A1* | 5/2007 | Ravo | A61B 1/00154 600/128 |
| 2007/0173687 A1 | 7/2007 | Shima et al. | |
| 2008/0249357 A1* | 10/2008 | Soetermans | A61B 1/00105 600/114 |
| 2009/0299135 A1 | 12/2009 | Spivey | |
| 2018/0000321 A1* | 1/2018 | Wales | A61B 17/1285 |

FOREIGN PATENT DOCUMENTS

| | | |
|---|---|---|
| JP | 2008-067725 A | 3/2008 |
| JP | 6211232 B1 | 10/2017 |
| WO | 2004/105593 A1 | 12/2004 |
| WO | 2007/037335 A1 | 5/2007 |
| WO | 2017/109900 A1 | 6/2017 |

\* cited by examiner

ENDOSCOPE AND ENDOSCOPE SYSTEM

CROSS REFERENCE TO RELATED APPLICATION

This application is a continuation application of PCT/JP2018/029834 filed on Aug. 8, 2018 and claims benefit of Japanese Application No. 2018-049127 filed in Japan on Mar. 16, 2018, the entire contents of which are incorporated herein by this reference.

BACKGROUND OF THE INVENTION

1. Field of the Invention

The present invention relates to an endoscope in which a channel tube is externally attached to an insertion portion, and an endoscope system.

2. Description of the Related Art

In an endoscope used in a medical field, an elongated insertion portion is inserted into a body cavity and treatment is performed under the endoscope.

Therefore, the insertion portion is provided with a treatment instrument channel configured to guide a treatment instrument into the body cavity.

In addition, there is an endoscope including a bending portion on a distal end side of the insertion portion so that a position of a distal end portion is directed in a desired direction. The bending portion is bent by an operation of an operation device provided in an operation portion.

The insertion portion of the endoscope is provided with not only the treatment instrument channel described above but also an air feeding/water feeding channel configured to remove dirt from an observation window and a front water feeding channel configured to spray a cleaning solution toward an affected area to clean a mucous membrane, etc., adhering to the affected area.

The treatment instrument channel also serves as a fluid conduit for suction or water feeding. For this reason, when the treatment instrument is inserted into the treatment instrument channel, the suction amount or the water feeding amount is reduced. Such a defect can be solved when anew treatment instrument channel is provided in the insertion portion. However, when a new treatment instrument channel is provided in the insertion portion, a cross-sectional area of the insertion portion increases. In other words, it is difficult to reduce a diameter of the insertion portion.

Japanese Patent Application Laid-Open Publication No. 11-192203 discloses an externally attached channel tube that can be bent relatively flexibly. The externally attached channel tube is attached to an outer peripheral surface of an insertion portion in a longitudinal axis direction of the insertion portion. Such an externally attached channel tube is attached to a bending portion with, for example, a rubber band, a tongue piece is fixed onto a distal end portion with a fixing tape, or an attaching cap is engaged with the distal end portion.

According to the externally attached channel tube, the defect that the cross-sectional area of the insertion portion increases can be solved, and the number of channels can be increased.

SUMMARY OF THE INVENTION

An endoscope of one aspect of the present invention includes: an insertion portion configured to be inserted into a subject; and a channel fixing portion disposed on an outer periphery of the insertion portion and configured such that a part or all of a channel tube having a long length is fixed in a state of being embedded in a distal end portion of the insertion portion.

An endoscope system of another aspect of the present invention includes: an endoscope including an insertion portion configured to be inserted into a subject and a channel fixing portion disposed on an outer periphery of the insertion portion and configured such that a part or all of a channel tube having a long length is fixed in a state of being embedded in a distal end portion of the insertion portion; and the channel tube, wherein a tube distal end portion of the channel tube includes a tube distal end-side inclination surface having a tapered outer shape.

An endoscope system of another aspect of the present invention includes: a detachable channel tube including a cap body having a tubular shape and detachably disposed on an outer periphery of a distal end portion of an insertion portion, and a long channel tube extending from the cap body and including a penetration hole along a longitudinal axis; and an endoscope including an insertion portion configured to be inserted into a subject, and a tube disposing portion provided on an outer peripheral surface side of a distal end portion of the insertion portion and including a concave groove in which the channel tube formed in the cap body is embedded and disposed.

DETAILED DESCRIPTION OF THE PREFERRED EMBODIMENT

Figure 1:
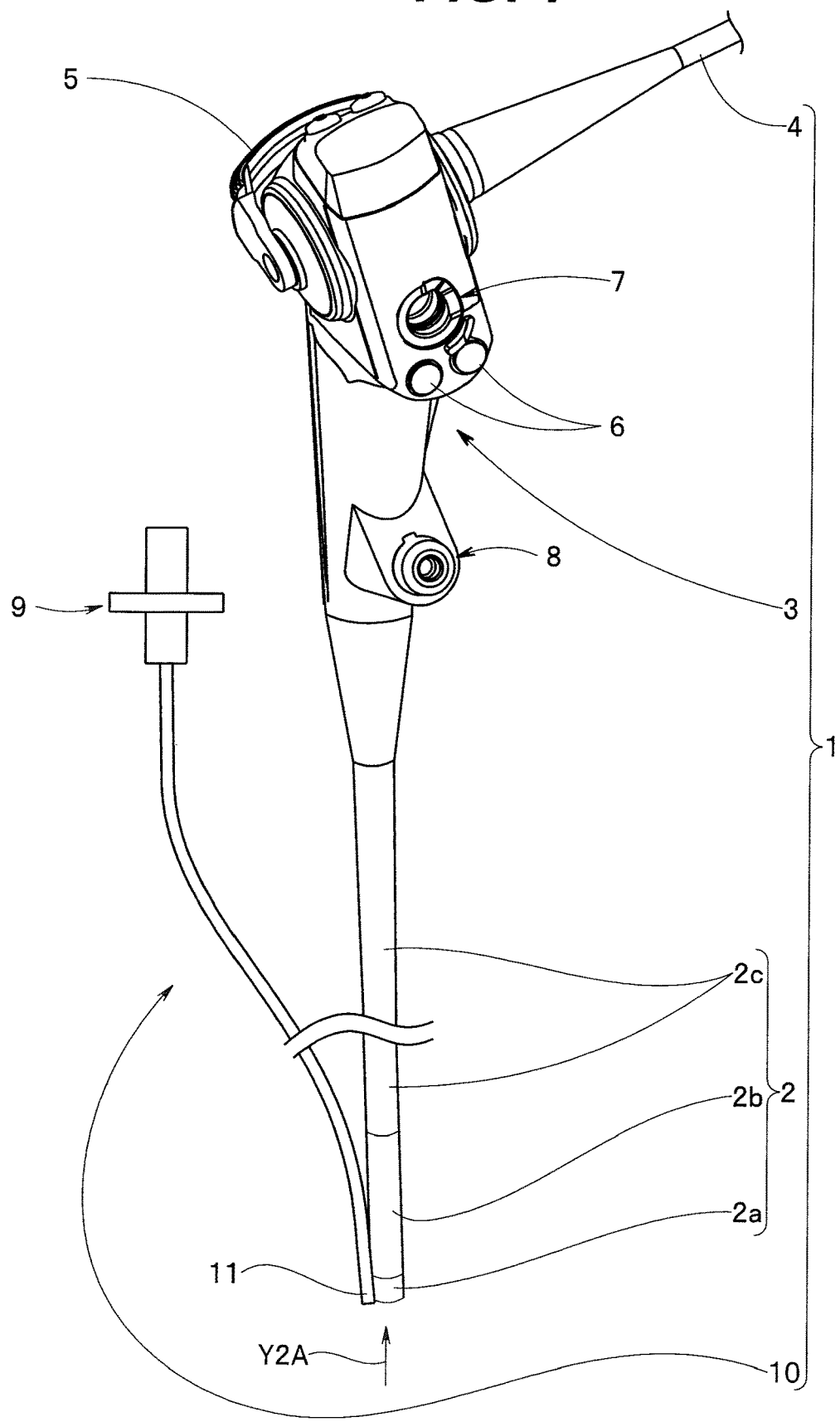
FIG. 1 is a view illustrating an endoscope including an insertion portion and a channel tube disposed on an outer peripheral surface side of the insertion portion.

An embodiment of the present invention will be described below with reference to the drawings.

Note that, in each of the drawings used in the following description, scales are varied for each component to show the respective components in recognizable sizes in the drawings. In other words, the present invention is not limited only to numbers of the components, shapes of the components, ratios of sizes of the components, and relative positional relations among the respective components shown in the drawings.

As shown in FIG. 1, an endoscope 1 includes an insertion portion 2, an operation portion 3, a universal cable 4, and a channel tube 10. In other words, the endoscope 1 is an endoscope equipped with a channel tube.

The insertion portion 2 is an elongated member that is inserted into a subject being a site to be observed. The channel tube 10 is provided to be located on an outer peripheral side of the insertion portion 2.

The insertion portion 2 includes an insertion portion distal end portion (hereinafter, abbreviated as a distal end portion) 2a, a bending portion 2b, and a flexible tube portion 2c that are continuously provided in order from a distal end side.

The bending portion 2b is configured to be bendable in two directions, for example, up and down. The flexible tube portion 2c is a long tubular member having flexibility.

The bending portion 2b may be configured to be bendable in four directions of up, down, left, and right. In addition, the insertion portion 2 may have a configuration in which a rigid tube portion is continuously provided on a proximal end side of the bending portion 2b instead of the flexible tube portion 2c.

The operation portion 3 is provided with a bending operation portion 5, various switches 6, a suction cylinder 7, and a treatment instrument insertion port 8. The bending operation portion 5 is operated to bend the bending portion 2b. Various switches 6 are, for example, a release switch, a freeze switch, and an observation mode changeover switch that performs a changeover between normal observation and fluorescence observation.

A suction button (not shown) is disposed on the suction cylinder 7. The treatment instrument insertion port 8 communicates with an opening for treatment instrument channel (see reference numeral 23 in FIG. 2A) of the distal end portion 2a through a channel tube for treatment instrument insertion (see reference numeral 26b in FIG. 2B). The channel tube for treatment instrument insertion also serves as a fluid channel for suction or water feeding. Accordingly, the opening for treatment instrument channel 23 also serves as a suction port or a water feeding port.

The universal cable 4 extends from a side portion of the operation portion 3. An endoscope connector (not shown) is provided at an end portion of the universal cable 4. The endoscope connector is detachably attached to an external apparatus, for example, a camera control unit including a light source apparatus.

The channel tube 10 is made of resin or rubber having a predetermined flexibility. The channel tube 10 is long with a predetermined outer diameter and includes a penetration hole (see reference numeral 12 in FIG. 2B) penetrating along a longitudinal axis. The channel tube 10 is fixed to the distal end portion 2a. In the present embodiment, a tube distal end portion 11, which is a part of the channel tube 10, is fixed to the distal end portion 2a.

In the present embodiment, a channel tube proximal end side portion (hereinafter, referred to as a tube proximal end side portion) 13 on a proximal end side from the tube distal end portion 11 fixed to the distal end portion 2a is movable along an outer periphery of the insertion portion 2. Reference numeral 14 denotes a tube distal end surface, and the tube distal end surface 14 is disposed on substantially the same plane as a distal end surface 20 of the insertion portion 2.

Reference numeral 9 denotes a channel port, which is attached to a proximal end portion of the channel tube 10.

Figure 2A:
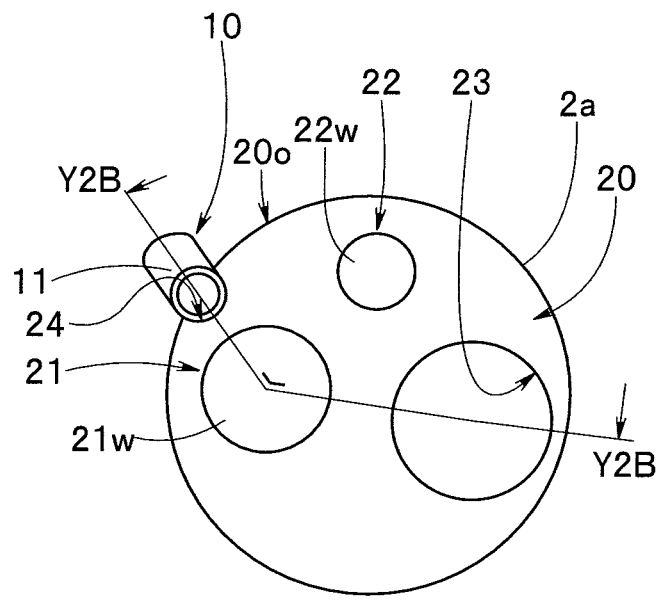
FIG. 2A is a view illustrating a distal end surface of the insertion portion and showing the distal end surface of the insertion portion as viewed in a direction of an arrow Y2A in FIG. 1.

As shown in FIG. 2A, the distal end surface 20 of the insertion portion 2 is provided with an observation window 21w of an image pickup optical system 21 and an illumination window 22w of an illuminating optical system 22. Reference numeral 23 denotes an opening for treatment instrument channel, which also serves as a suction opening or a water feeding opening.

The tube distal end portion 11 of the channel tube 10 is fixed to a channel fixing portion 24 provided at the distal end portion 2a. The channel fixing portion 24 is a concave groove recessed with respect to a distal-end-portion outer peripheral surface 20o of the distal end portion 2a. A part or all of the tube distal end portion having a circular section is embedded in the concave groove. In the present embodiment, the concave groove of the channel fixing portion 24 has substantially a semicircular shape and is a curved surface that substantially coincides with an outer surface of the channel tube 10.

Figure 2B:
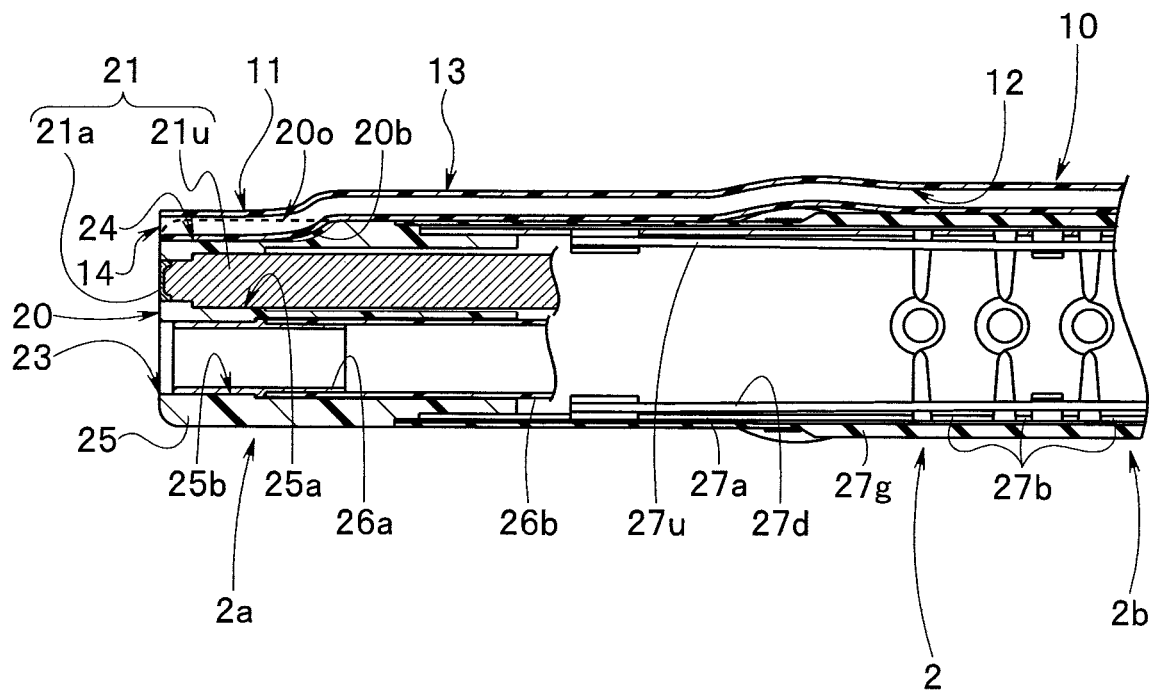
FIG. 2B is a cross-sectional view taken along a line Y2B-Y2B in FIG. 2A and illustrating a relation between the insertion portion and the channel tube.

Reference numeral 25 shown in FIG. 2B denotes a rigid distal end portion. The rigid distal end portion 25 configures the distal end portion 2a of the insertion portion 2. The rigid distal end portion 25 is provided with a penetration hole for observation optical system 25a, a penetration hole for treatment instrument channel 25b, and a penetration hole for illuminating optical system (not shown).

As shown in FIGS. 2A and 2B, the penetration hole for observation optical system 25a is provided with the image pickup unit 21u including the observation window 21w configuring the image pickup optical system, an image pickup device (not shown), and an objective optical system (not shown). On the other hand, a distal end portion of a pipe sleeve 26a is fixed to the penetration hole for treatment instrument channel 25b. One end portion of the treatment instrument channel tube 26b is fixed to a proximal end portion of the pipe sleeve 26a. The illumination window 22w and an LED illumination (not shown) are fixed to the penetration hole for illuminating optical system.

In the present embodiment, the opening for treatment instrument channel 23, the penetration hole for treatment instrument channel 25b, the pipe sleeve 26a, and the treatment instrument channel tube 26b configure a channel for treatment instrument insertion that also serves as a fluid channel.

As shown in FIG. 2B, a distal end side of a distal end bending piece 27a configuring the bending portion 2b is integrally fixed to the proximal end side of the rigid distal end portion 25. Reference numeral 27b denotes a plurality of bending pieces connected to the distal end bending piece 27a. The bending portion 2b includes these bending pieces 27a and 27b and a bending rubber 27g that covers the bending pieces 27a and 27b. A distal end portion of an upper bending wire 27u and a distal end portion of a lower bending wire 27d are fixed at predetermined positions of the distal end bending piece 27a, respectively.

Figure 2C:
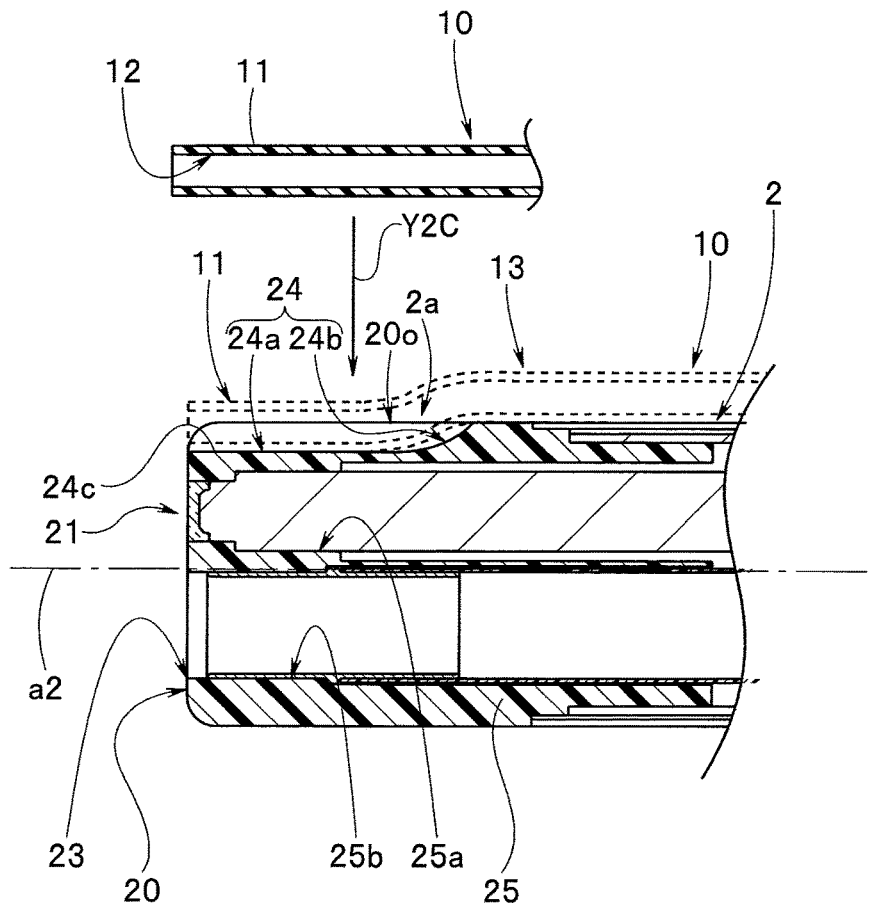
FIG. 2C is an enlarged view of a distal end side of the insertion portion, and is a view illustrating a channel fixing portion provided at the distal end portion and a tube distal end portion of a channel tube fixed to the channel fixing portion.

As shown in FIG. 2C, the channel fixing portion 24 includes a tube distal end portion fixing surface 24a and a guide surface 24b.

The tube distal end portion fixing surface 24a is provided on the distal end surface 20 side, and is recessed in a predetermined size with respect to the distal-end-portion outer peripheral surface 20o. In other words, a bottom portion 24c of the tube distal end portion fixing surface 24a is parallel to a longitudinal axis a2 of the insertion portion 2.

The guide surface 24b is a curved surface by which the tube distal end portion 11 is smoothly guided from the tube distal end portion fixing surface 24a toward the outer peripheral surface of the insertion portion 2.

The tube distal end portion 11 of the channel tube 10 is disposed on the tube distal end portion fixing surface 24a and the guide surface 24b of the channel fixing portion 24 as shown by an arrow Y2C in FIG. 2C.

In the present embodiment, as shown by a broken line in FIG. 2C, the tube distal end portion 11 is disposed on the tube distal end portion fixing surface 24a and the guide surface 24b. The tube distal end portion 11 is disposed such that a part or all of the outer peripheral surface is embedded in the channel fixing portion 24. On the other hand, the tube distal end portion 11 is disposed on the guide surface 24b, and is led out on the outer peripheral surface of the insertion portion 2.

The tube distal end portion 11 is fixed in a state of being embedded in the distal end portion 2a with an adhesive (see reference numeral 20b in FIG. 2B), for example. In the fixed state, the tube proximal end side portion 13 located on the proximal end side relative to the tube distal end portion 11 embedded and fixed in the distal end portion 2a is independent of the insertion portion 2. For this reason, the tube proximal end side portion 13 is movable with respect to the insertion portion 2.

In this way, the distal end portion 2a of the insertion portion 2 is provided with the tube distal end portion fixing surface 24a recessed in a predetermined size with respect to the distal-end-portion outer peripheral surface 20o. Then, the tube distal end portion 11 is fixed to the tube distal end portion fixing surface 24a, and the tube distal end portion 11 of the channel tube 10 is embedded and fixed in the distal end portion 2a.

Thus, the amount of protrusion of the tube distal end portion 11 fixed to the tube distal end portion fixing surface 24a of the channel fixing portion 24 from the distal-end-portion outer peripheral surface 20o is reduced by the embedded amount compared with the state in which the tube distal end portion 11 is fixed onto the distal-end-portion outer peripheral surface 20o. In other words, an outer diameter of the distal end portion 2a is prevented from being thicker by an outer diameter of the channel tube 10 even though a part of the channel tube 10 is fixed to the distal end portion 2a.

In addition, the tube proximal end side portion 13 is movable with respect to the outer peripheral surface of the insertion portion 2. Therefore, an outer diameter of the bending portion 2b and an outer diameter of the flexible tube portion 2c in the insertion portion 2 do not change to a large diameter. Accordingly, when the insertion portion 2 is inserted toward a core portion inside a body cavity, a position of the tube proximal end side portion 13 is freely changed according to the shape of the body cavity, and a bad influence on insertion property due to the provision of the channel tube 10 is reduced. The insertion property of the insertion portion 2 can be further improved.

In the embodiment described above, a part of the tube distal end portion 11 protrudes from the distal-end-portion outer peripheral surface 20o in the fixed state where a part of the channel tube 10 is embedded in the tube distal end portion fixing surface 24a recessed in the predetermined size with respect to the distal-end-portion outer peripheral surface 20o.

However, the tube distal end portion 11 may be completely embedded in the channel fixing portion 24 in the fixed state where the tube distal end portion 11 is embedded in the tube distal end portion fixing surface 24a. In other words, the concave groove of the channel fixing portion 24 is not limited to a substantially semicircular shape, but may be a concave groove in which a depth and a width are set to be larger in size than the outer diameter of the channel tube 10 in advance or a concave groove having a D-cut shape.

According to such a configuration, a defect is cleared that the outer diameter of the distal end portion 2a, to which the tube distal end portion 11 is fixed, becomes large due to the provision of the channel tube 10, and thus the diameter of the insertion portion 2 can be further reduced and the insertion property of the insertion portion 2 can be further improved.

In the embodiment described above, one channel fixing portion 24 is provided at the distal end portion 2a, and the tube distal end portion 11 of the channel tube 10 is embedded in the channel fixing portion 24. However, the number of channel fixing portions 24 provided at the distal end portion 2a is not limited to one, and may be two or more.

Figure 2D:
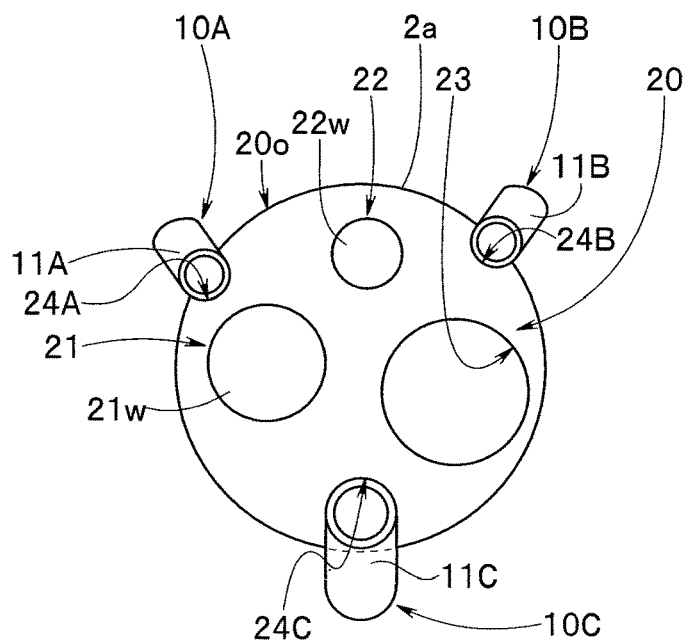
FIG. 2D is a view illustrating an endoscope in which a tube distal end portion of a channel tube is embedded and fixed in a plurality of channel fixing portions provided at the distal end portion.

For example, as shown in FIG. 2D, a plurality of channel fixing portions 24A, 24B, and 24C are provided at the distal end portion 2a, and tube distal end portions 11A, 11B, and 11C of channel tubes 10A, 10B, and 10C are fixedly provided to be embedded in the channel fixing portions 24A, 24B, and 24C, respectively.

An outer diameter of the third channel tube 10C is larger than outer diameters of the other channel tubes 10A and 10B. In addition, a concave groove of the first channel fixing portion 24A and a concave groove of the second channel fixing portion 24B have substantially a semicircular shape, and a depth of a concave groove of the third channel fixing portion 24C is set to be larger than an outer diameter of the tube distal end portion 11C.

According to such a configuration, since the plurality of channel tubes are provided on the outer peripheral side of the insertion portion 2, an endoscope 1 having excellent insertion property and treatment property can be realized.

In the configuration described above, among the plurality of tube distal end portions, a predetermined number of tube distal end portions protrude from the distal-end-portion outer peripheral surface 20o, and a predetermined number of tube distal end portions do not protrude from the distal-end-portion outer peripheral surface 20o. However, all of the tube distal end portions may protrude from the distal-end-portion outer peripheral surface 20o, or any of the tube distal end portions may not protrude from the distal-end-portion outer peripheral surface 20o.

Another configuration example of the channel tube will be described with reference to FIGS. 3A and 3B.

Figure 3A:
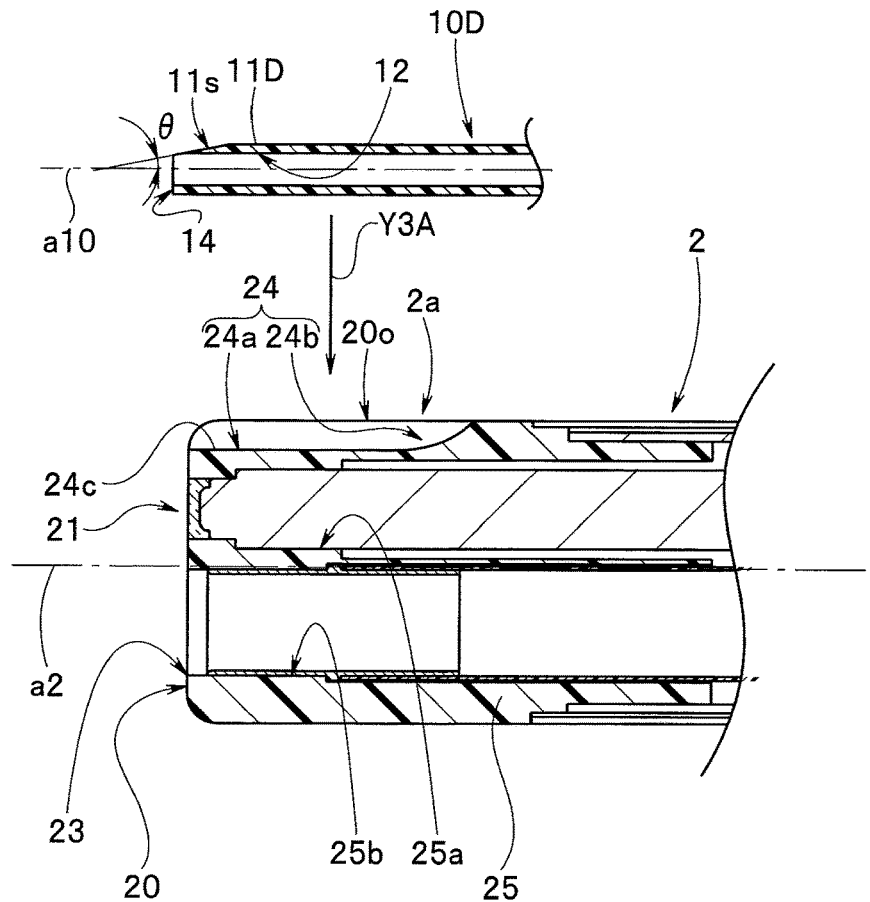
FIG. 3A shows another configuration example of the channel tube, which is a view illustrating a channel tube including an inclination surface at the tube distal end portion.

As shown in FIG. 3A, the channel tube 10D of the present embodiment includes a tube distal end-side inclination surface (hereinafter, referred to as a tube inclination surface) 11s at a predetermined position of the tube distal end portion on the tube distal end surface 14 side. The tube inclination surface 11s intersects a tube center axis a10 extending toward the distal end side from the tube distal end surface 14 at a predetermined angle θ. Therefore, an outer shape of the tube distal end portion 11D of the channel tube 10D is a tapered shape in which the outer shape continuously decreases toward the tube distal end surface 14.

Figure 3B:
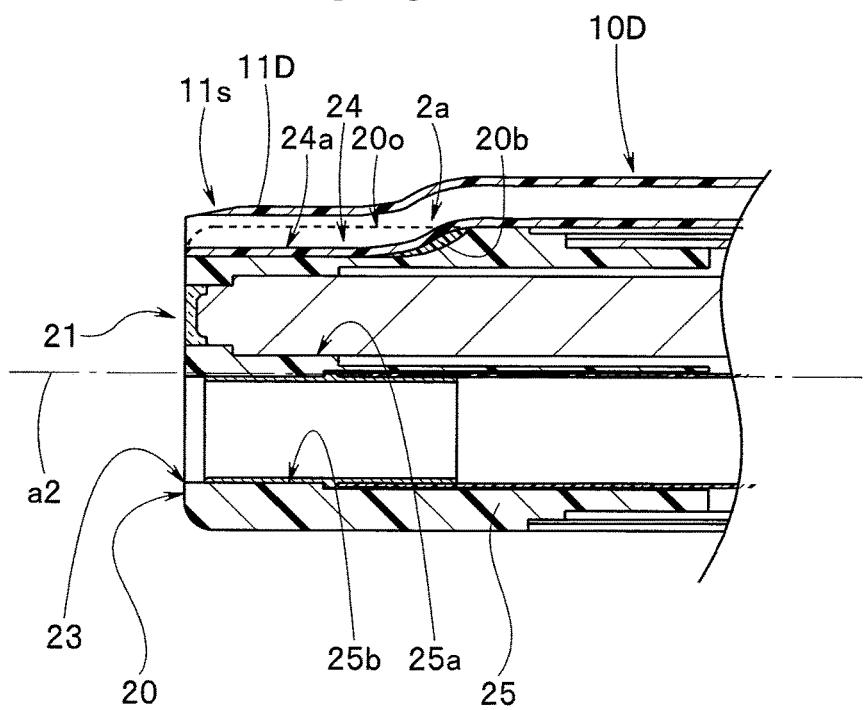
FIG. 3B is a view illustrating a state where the tube distal end portion having the inclination surface is fixed to the channel fixing portion

The tube distal end portion 11D is disposed on a tube distal end portion fixing surface 24a as shown by an arrow Y3A in FIG. 3A, and then fixed to a channel fixing portion 24 with an adhesive 20b as shown in FIG. 3B. In the fixed state, the tube inclination surface 11s of the tube distal end portion 11D is disposed on the distal-end-portion outer peripheral surface 20o side opposite to the bottom portion 24c of the tube distal end portion fixing surface 24a.

In this way, the tube inclination surface 11s is provided at the tube distal end portion 11D of the channel tube 10D disposed in the channel fixing portion 24 recessed in the distal end portion 2a of the insertion portion 2. Then, the tube inclination surface 11s is disposed on the distal-end-portion outer peripheral surface 20o side as described above, and the tube distal end portion 11D is embedded and fixed in the channel fixing portion 24.

As a result, in the state where the tube distal end portion 11D including the tube inclination surface 11s is fixed to the channel fixing portion 24, protruding shape of the tube distal end portion 11D protruding from the distal-end-portion outer peripheral surface 20o becomes smaller on the distal end surface 20 side as compared with the bending portion 2b side.

According to such a configuration, in the state where the tube distal end portion 11D of the channel tube 10D is embedded and fixed in the channel fixing portion 24, the outer shape of the distal end portion 2a of the insertion portion 2 is formed in a tapered shape, thereby the diameter of the insertion portion 2 can be reduced and the insertion property of the insertion portion 2 can be further improved.

Further another configuration example of the channel fixing portion will be described with reference to FIGS. 4A and 4B.

Figure 4A:
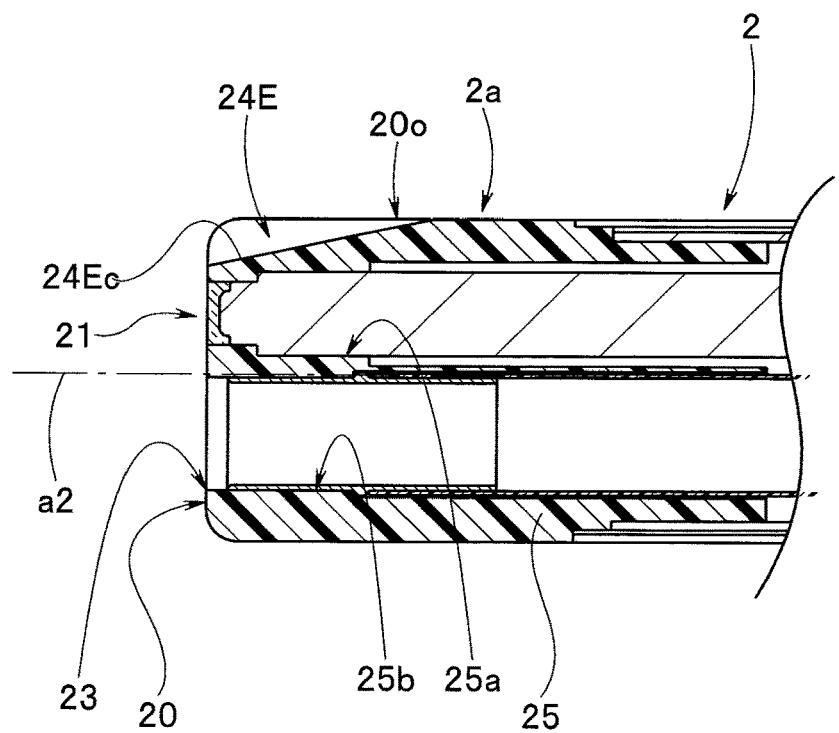
FIG. 4A shows another configuration example of the channel fixing portion, which is a view illustrating a channel fixing portion inclined with respect to a longitudinal axis of the insertion portion.
Figure 4B:
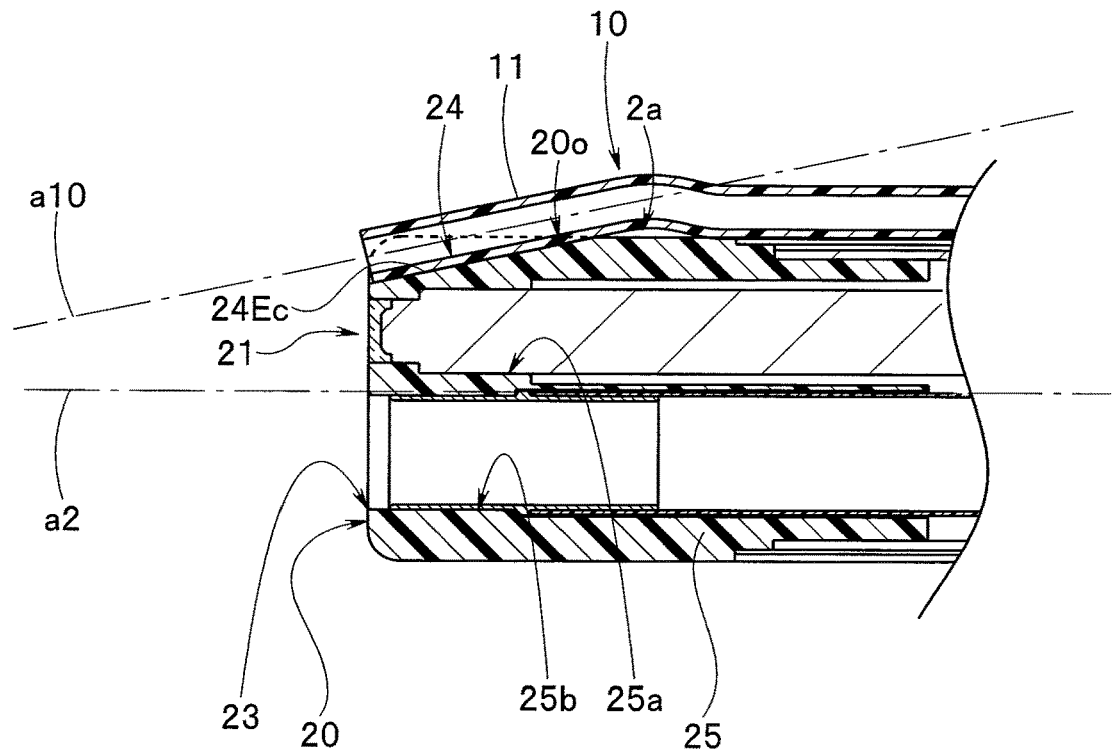
FIG. 4B is a view illustrating a state where the tube distal end portion is fixed to the channel fixing portion inclined with respect to the longitudinal axis of the insertion portion.

As shown in FIG. 4A, a channel fixing portion 24E of the present embodiment provided at the distal end portion 2a is a concave groove recessed with respect to the distal-end-portion outer peripheral surface 20o, and a bottom portion 24Ec of the concave groove is inclined with respect to the longitudinal axis a2 of the insertion portion 2. In the present embodiment, the tube distal end portion 11 of the channel tube 10 is fixed to the channel fixing portion 24E as shown in FIG. 4B.

In the fixed state, a tube center axis a10 of the channel tube 10 is inclined with respect to the longitudinal axis a2 of the insertion portion 2. Specifically, the tube center axis a10 of the channel tube 10 gradually approaches closer to the longitudinal axis a2 from the distal-end-portion outer peripheral surface 20o as going in the insertion direction of the insertion portion which is in front of the distal end surface 20 of the insertion portion 2.

In other words, the tube center axis a10 of the channel tube 10 fixed to the channel fixing portion 24E formed to be inclined with respect to the longitudinal axis a2 is inclined to gradually grow apart from the longitudinal axis a2 as going toward the insertion portion proximal end side from the distal end surface 20. In other words, the tube center axis a10 of the channel tube 10 is inclined in an inner diameter direction of the insertion portion 2 as going in the insertion direction of the insertion portion which is in front of the distal end surface 20 of the insertion portion 2.

In this way, a bottom portion 24Ec of the channel fixing portion 24E recessed in the distal end portion 2a of the insertion portion 2 is inclined with respect to the longitudinal axis a2 of the insertion portion 2. Then, the tube distal end portion 11 of the channel tube 10 is fixed to the channel fixing portion 24E inclined with respect to the longitudinal axis a2, and the tube center axis a10 is inclined with respect to the longitudinal axis a2.

Thus, the outer shape of the distal end portion 2a formed integrally with the tube distal end portion 11 becomes smaller according to the inclination from the bending portion 2b toward the distal end surface 20.

According to such a configuration, in the state where the inclination surface is not provided at the tube distal end portion 11 of the channel tube 10 and the tube distal end portion 11 is embedded and fixed in the channel fixing portion 24E, the outer shape of the distal end portion 2a of the insertion portion 2 is formed in a tapered shape, so that the diameter of the insertion portion 2 can be reduced and the insertion property of the insertion portion 2 can be improved.

In the embodiment described above, the tube center axis a10 of the channel tube 10 is inclined to gradually approach closer to the longitudinal axis a2 from the distal-end-portion outer peripheral surface 20o as going in the insertion direction of the insertion portion from the distal end surface 20 of the insertion portion 2, thereby the insertion property is improved. However, the inclination direction and the inclination angle of the tube center axis a10 of the channel tube 10 may be set as shown in FIG. 5A.

Figure 5A:
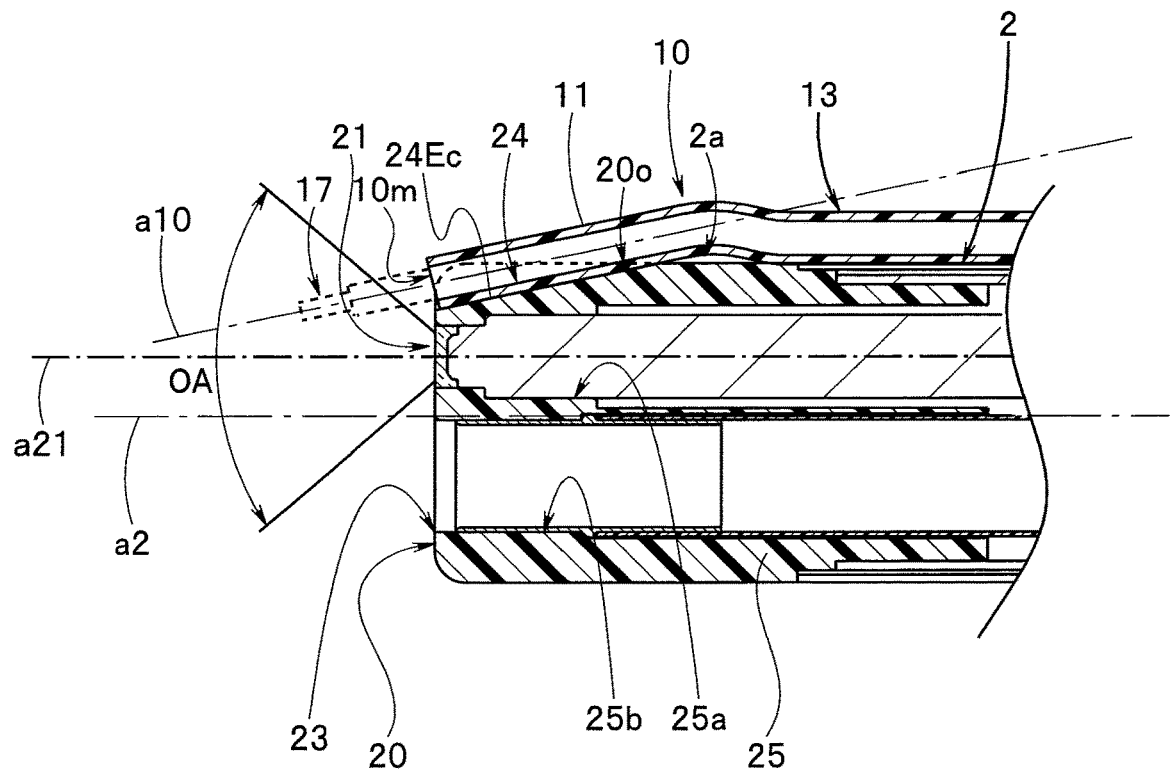
FIG. 5A is a view illustrating a state where a tube center axis of the channel tube is inclined with respect to an optical axis of an image pickup optical system and the tube center axis is inclined to approach the longitudinal axis from a distal-end-portion outer peripheral surface side as going in an insertion direction of the insertion portion from the distal end surface and is inclined toward a field of view of the image pickup optical system.

As shown in FIG. 5A, the tube center axis a10 of the channel tube 10 of the present embodiment is inclined with respect to an optical axis a21 of the image pickup optical system 21. Specifically, the tube center axis a10 is inclined to gradually approach the longitudinal axis a2 from the distal-end-portion outer peripheral surface 20o side as going in the insertion direction of the insertion portion from the distal end surface 20 of the insertion portion 2, and is inclined toward a desired position within a field of view OA of the image pickup optical system 21.

Figure 5B:
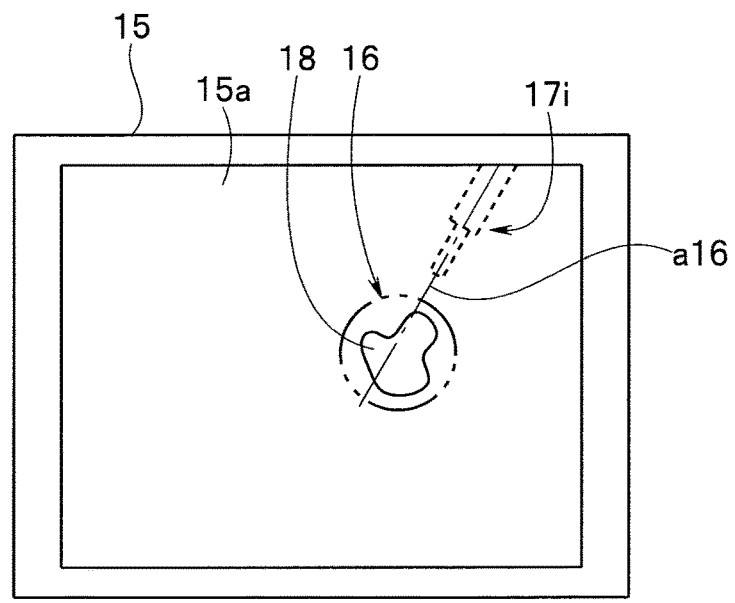
FIG. 5B is a view illustrating the tube center axis of the channel tube in which an inclination direction and an inclination angle are set such that the tube center axis is inclined toward a region, which is indicated by a two-dot chain line, on an observation screen of a display apparatus.

Specifically, the inclination direction and the inclination angle of the tube center axis a10 may be set such that the tube center axis a10 is inclined toward, for example, a region 16, which is indicated by a two-dot chain line, in an observation image of the endoscope displayed on an observation screen 15a of a display apparatus 15 shown in FIG. 5B. Reference numeral a16 denotes a virtual tube center axis, which is a virtual line indicating the tube center axis on the observation screen 15a.

According to such a configuration, a treatment instrument 17 (see a two-dot chain line) led out of a distal end opening 10m of the channel tube 10 shown in FIG. 5A penetrates into the field of view OA, and thus a treatment instrument image 17i indicated by a broken line is displayed on the observation screen 15a.

When the treatment instrument 17 is, for example, a laser fiber, a calculus 18 is displayed in a vicinity of the region 16 of the observation screen 15a. In such a display state, a doctor leads out the laser fiber from a distal end opening 10m. Then, the laser fiber advances toward the calculus 18 along the virtual tube center axis a16 on the observation screen 15a. Then, the doctor allows a fiber distal end to face the calculus 18 with a desired positional relation and performs a crushing treatment.

According to such a configuration, the doctor allows the fiber distal end of the laser fiber to face the calculus 18 smoothly and with high accuracy and can perform the crushing treatment.

In this way, the inclination direction and the inclination angle are set such that the tube center axis a1 of the channel tube 10 is inclined to gradually approach the longitudinal axis a2 from the distal-end-portion outer peripheral surface 20o side as going in the insertion direction of the insertion portion from the distal end surface 20 of the insertion portion 2, and is inclined toward a desired position. As a result, the outer shape of the distal end portion 2a can be formed in the tapered shape to improve workability such as treatment and sampling in addition to the reduction in diameter of the insertion portion 2 and the improvement of the insertion property.

In the embodiment described above, for example, as shown in FIG. 2B, the tube distal end surface 14 of the channel tube 10 is disposed on substantially the same plane as the distal end surface 20 of the insertion portion 2. However, the position where the tube distal end surface 14 is disposed with respect to the distal end surface 20 is not limited to substantially the same plane, and a tube distal end surface 14F may also protrude from the distal end surface 20 as in a channel tube 10F shown in FIG. 6A, for example.

In such a protruding state, the tube distal end surface 14F is disposed within the field of view OA in advance. Then, the tube distal end side of the protruding channel tube 10F is displayed on the observation screen. Thereby, when the insertion portion 2 is inserted into the core portion in the body cavity, it is possible to confirm the position of the tube distal end surface 14F of the channel tube 10F and to advance the insertion portion 2.

Figure 6A:
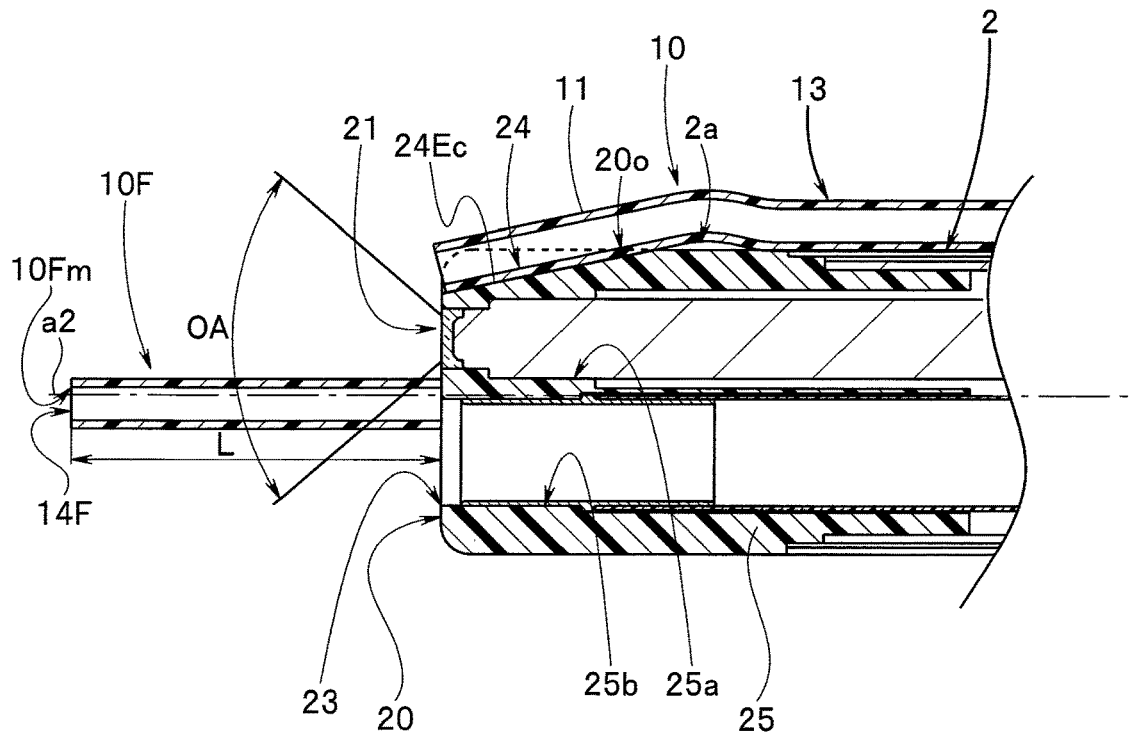
FIG. 6A is a view illustrating an endoscope including a channel tube in which a tube distal end surface protrudes from the distal end surface.

As shown in FIG. 6A, the tube distal end surface 14F of the channel tube 10F protrudes from the distal end surface 20 by a distance L in the insertion direction of the insertion portion. Therefore, in the present embodiment, a tube middle portion (not shown), which is a part of the channel tube 10F, is embedded in the channel fixing portion 24 and is fixed to the distal end portion 2a.

The channel tube 10F described above is a water feeding tube, for example.

According to such a configuration, when a distal end opening 10Fm of the channel tube 10F functions as the water feeding port and the opening for treatment instrument channel 23 functions as a suction port, the water feeding port is displaced from the suction port to the distal end side in the longitudinal axis a2. As a result, for example, since water starts to be fed from the water feeding port and the water starts to be sucked from the suction port, the water to be fed can efficiently flow from the water feeding port toward the suction port.

Figure 6B:
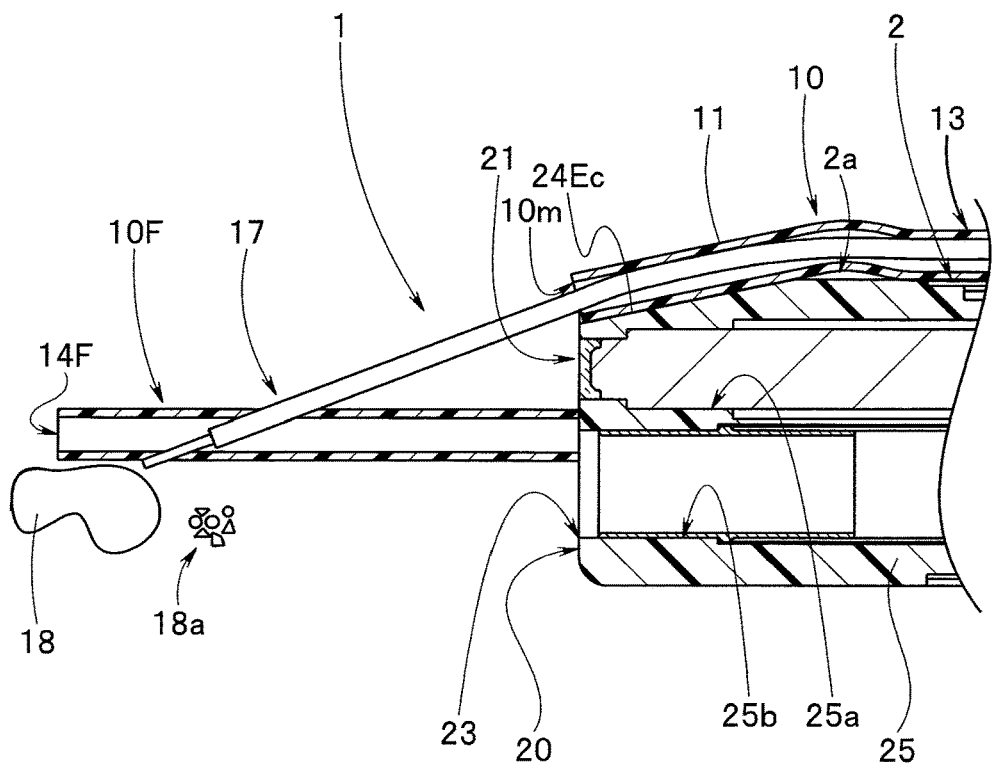
FIG. 6B is a view illustrating an operation of the endoscope in a state where the protruding channel tube is used as a water feeding tube.

An endoscope 1 is configured as shown in FIG. 6B.

The first channel tube 10 serving as the treatment instrument tube and the second channel tube 10F serving as the water feeding tube are fixed to the distal end portion 2a of the insertion portion 2 in the endoscope 1 shown in FIG. 6B. As shown in the drawing, the tube distal end surface 14F of the second channel tube 10F protrudes from the distal end surface 20 by a predetermined distance. In addition, the opening for treatment instrument channel 23 functions as a suction port as described above.

According to the endoscope 1 having such a configuration, it is possible to crush and extract a urinary calculus in the following steps, for example.

First, the doctor allows insertion of the insertion portion 2 of the endoscope 1 including the channel tubes 10 and 10F into a urinary tract. Then, the doctor allows the urinary calculus to be displayed at a predetermined region on the observation screen as described above.

Next, the doctor allows insertion of the laser fiber into the first channel tube 10, allows the fiber distal end surface to face the urinary calculus, and crushes the calculus with irradiation of a laser beam. In addition, the doctor feeds water from the second channel tube 10F, and sucks the water and crushed pieces 18a through the opening for treatment instrument channel 23 of the insertion portion 2.

The tube distal end surface 14F of the second channel tube 10F protrudes from the distal end surface 20 of the insertion portion 2 in the insertion direction of the insertion portion in this way. Then, the laser fiber is led out from the first channel tube 10 to crush the urinary calculus. Further, water is supplied from the second channel tube 10F, and the water is sucked through the opening for treatment instrument channel 23.

As a result, the crushed pieces 18a crushed by the laser fiber flow into the treatment instrument channel tube 26b together with the water flowing from the water feeding port of the tube distal end surface 14F toward the suction port of the distal end surface 20, and is extracted.

Thereby, it is possible to reduce the diameter of the insertion portion 2 in which the outer shape of the distal end portion 2a is tapered, to improve the insertion property, and to improve the procedure of crushing and removing the calculus.

In the embodiment described above, the insertion portion 2 of the endoscope 1 is provided with the treatment instrument insertion channel that also serves as a suction channel. However, the endoscope may be configured as shown in FIGS. 7A and 7B.

Figure 7A:
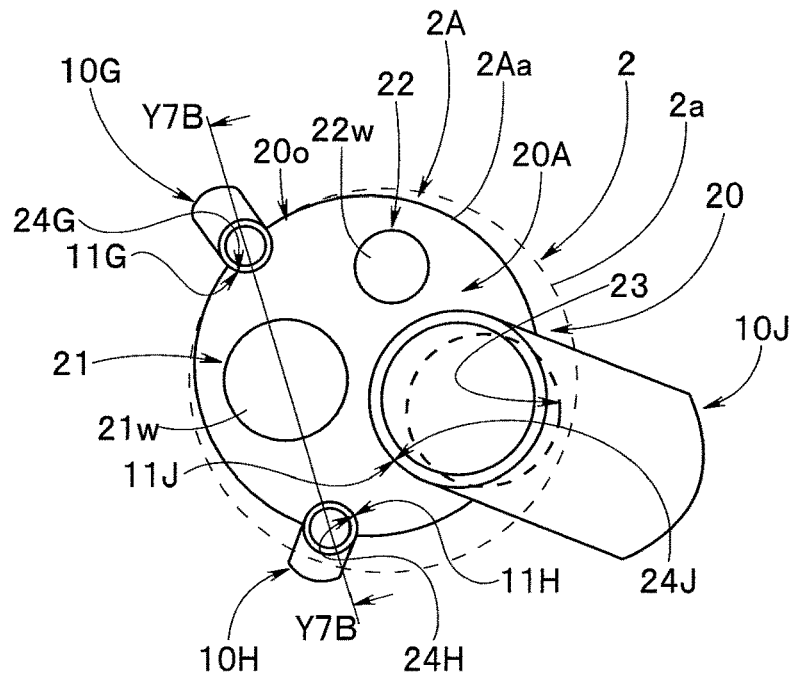
FIG. 7A is a front view illustrating an insertion portion in which a treatment instrument insertion channel also serving as a fluid channel is not provided in the insertion portion.
Figure 7B:
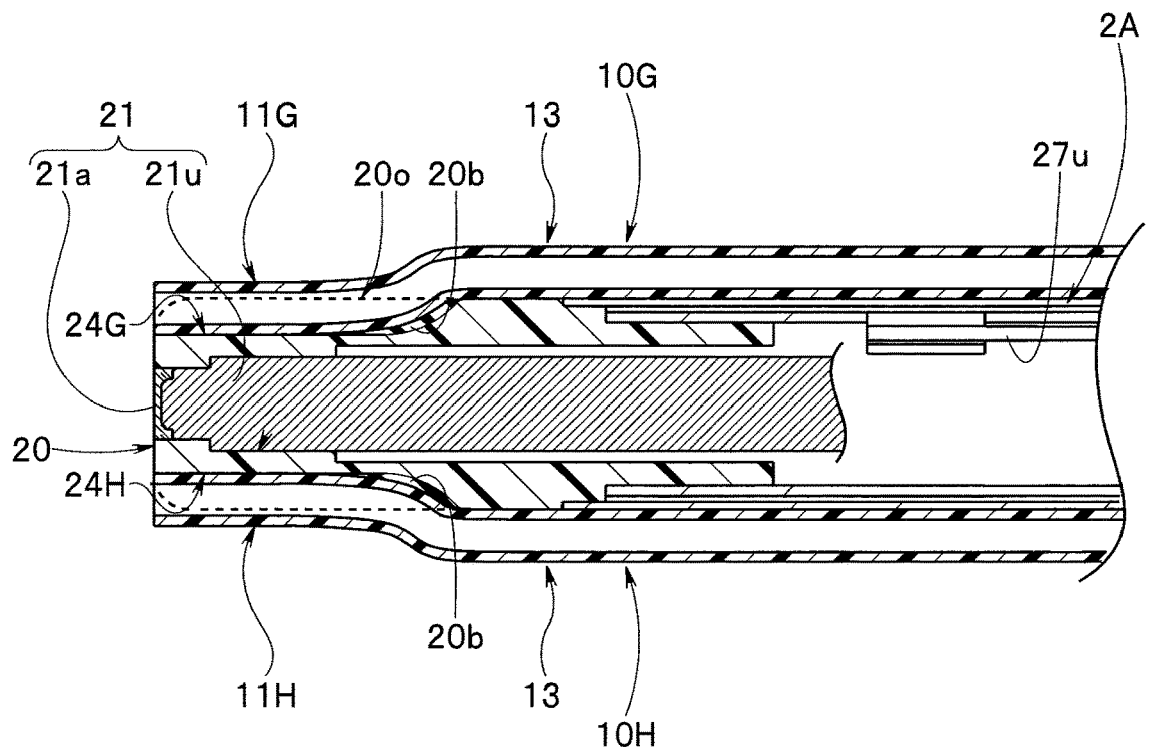
FIG. 7B is a cross-sectional view taken along a line Y7B-Y7B in FIG. 7A and illustrating an insertion portion in which a treatment instrument insertion channel also serving as a fluid channel is not provided in the insertion portion.

As shown in FIGS. 7A and 7B, the observation window 21w of the image pickup optical system 21 and the illumination window 22w of the illuminating optical system 22 are provided in a distal end surface 20A of a distal end portion 2Aa configuring an insertion portion 2A of the endoscope 1 according to the present embodiment. In addition, a plurality of channel fixing portions, for example, three channel fixing portions 24G, 24H, and 24J are provided on the distal-end-portion outer peripheral surface 20o of the distal end portion 2Aa at predetermined intervals in a circumferential direction.

In the present embodiment, the first channel fixing portion 24G is fixed with a first channel tube 10G that can serve as, for example, a treatment instrument tube, the second channel fixing portion 24H is fixed with a second channel tube 10H that can serve as, for example, a water feeding tube, and the third channel fixing portion 24J is fixed with a third channel tube 10J that can serve as, for example, a suction tube.

Accordingly, in the insertion portion 2A of the present embodiment, an opening of the third channel tube 10J provided to be located on the outer peripheral side of the insertion portion 2A is disposed as a suction opening, instead of the treatment instrument insertion channel that is inserted into the insertion portion 2 described above and also serves as the suction channel.

As described above, the endoscope 1 is configured in which the observation window 21w of the image pickup optical system 21 and the illumination window 22w of the illuminating optical system 22 are provided in the distal end surface 20A of the distal end portion 2Aa of the insertion portion 2A and the channel tubes 10G, 10H, and 10J are embedded and fixed in the tube fixing portions 24G, 24H, and 24J of the distal-end-portion outer peripheral surface 20o of the distal end portion 2Aa.

According to such a configuration, it is possible to reduce the outer diameter of the distal end portion 2Aa of the insertion portion 2A as compared with the distal end portion 2a of the insertion portion 2 provided with the image pickup optical system 21, the illuminating optical system 22, and the treatment instrument insertion channel 23 indicated by the broken line on the distal end surface 20 of the insertion portion 2.

In addition, the channel fixing portions 24G, 24H, and 24J are provided in the distal end portion 2Aa, the diameter of which is reduced, and tube distal end portions 11G, 11H, and 11J are embedded and fixed in the channel fixing portions 24G, 24H, and 24J, respectively.

As a result, although the tube distal end portions 11G, 11H, and 11J are fixed to the distal end portion 2Aa as described above, the outer diameter of the distal end portion 2Aa can be prevented from being thicker by the outer diameter of the tube distal end portions 11G, 11H, and 11J.

Further, since tube proximal end side portion 13 is movable along the outer peripheral surface of the insertion portion 2A as described above, the outer diameter of the bending portion 2b and the outer diameter of the flexible tube portion 2c in the insertion portion 2A are smaller than the outer diameter of the bending portion 2b and the outer diameter of the flexible tube portion 2c in the insertion portion 2.

As a result, it is possible to reduce the diameter of the insertion portion 2A provided with the channel tubes 10G, 10H, and 10J and to further improve the insertion property of the insertion portion 2.

The channel tubes, which are fixed to the channel fixing portions 24G, 24H, and 24J, respectively, are not limited to use for the treatment instrument tube, the water feeding tube, or the suction tube described above, and appropriately desired channel tubes are fixed depending on the purpose of use. Further, the number and the position of the channel fixing portions, and the outer diameter and the inner diameter of the channel tubes embedded and fixed in the channel fixing portions are also appropriately set depending on the purpose of use.

Figure 7C:
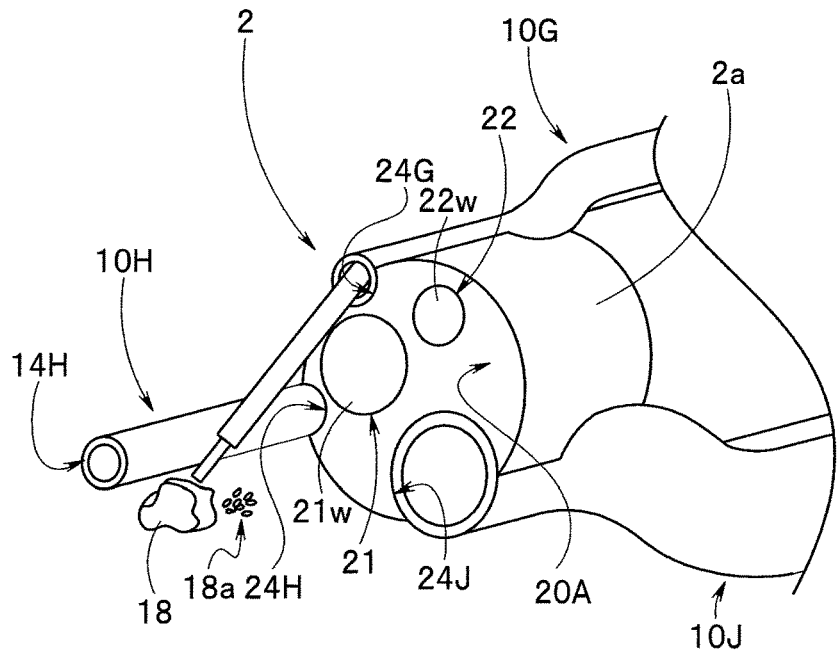
FIG. 7C is a view illustrating an operation of the endoscope in a state where the protruding channel tube is used as a water feeding tube.

As shown in FIG. 7C, an endoscope 2A is configured in which a tube distal end surface 14H of the channel tube 10H for water feeding protrudes from the distal end surface 20A by a predetermined distance in the insertion direction of the insertion portion.

According to such a configuration, similarly to the endoscope 1 shown in FIG. 6B described above, the doctor allows insertion of the laser fiber into the first channel tube 10G, allows the fiber distal end surface to face the urinary calculus, and crushes the calculus with irradiation of a laser beam.

In addition, the doctor feeds water from the water feeding port of the second channel tube 10H, and sucks the water through the suction port of the third channel tube 10J. As a result, the crushed pieces crushed by the laser fiber can flow into the third channel tube 10J together with the water flowing toward the suction port from the water feeding port, and the calculus can be extracted.

A channel tube, which is detachably attached to the insertion portion of the endoscope, will be described with reference to FIGS. 8A to 8C.

In the endoscope described above, the channel tube is embedded and fixed in the channel fixing portion provided at the distal end portion. An endoscope system 1A of the present embodiment includes a detachable channel tube 50 that is detachably attached to the distal end portion 2a of the insertion portion 2, as shown in FIG. 8A.

The detachable channel tube 50 is formed of an elastic member, and includes a cap portion 59, a first channel tube portion 51, and a second channel tube portion 52, the first and second channel tube portions extending from the cap portion 59. Each of the channel tube portions 51 and 52 is long and includes a penetration hole along a longitudinal axis.

Figure 8A:
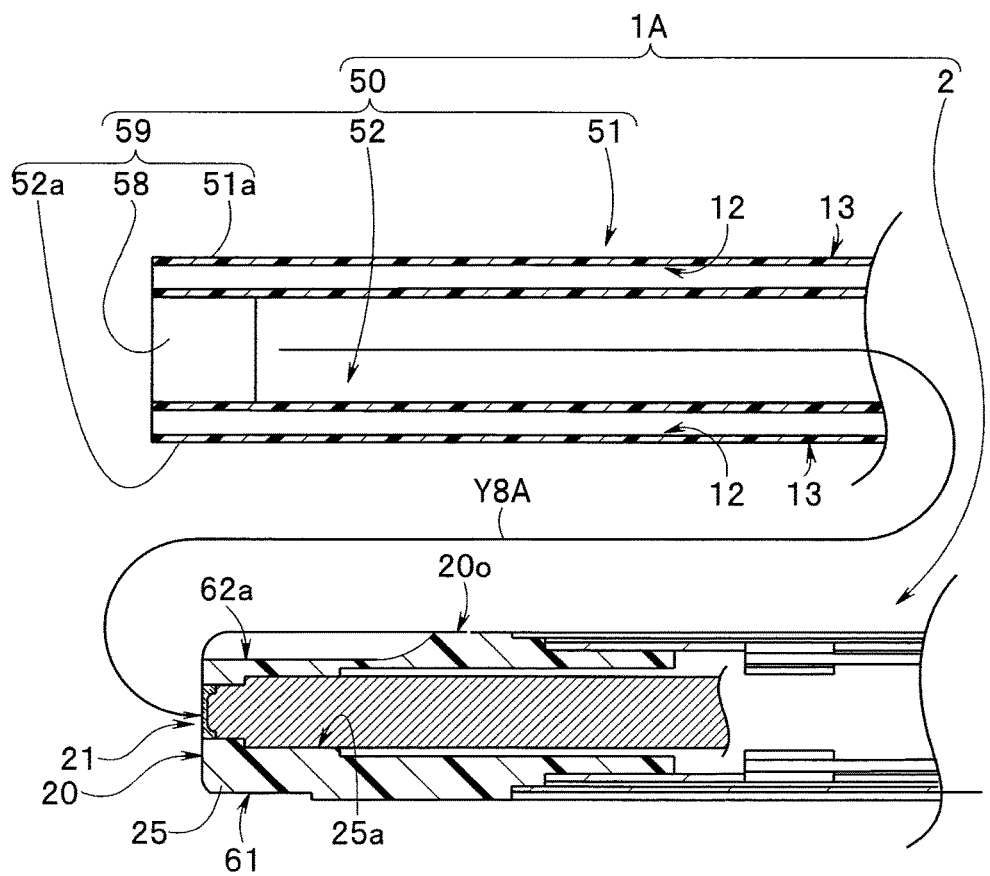
FIG. 8A is a view illustrating a detachable channel tube configuring an endoscope system and a cap mounting portion provided at the distal end portion of the insertion portion, in which the detachable channel tube is a cross-sectional view taken along a line Y8A-O-Y8A in FIG. 8B and the distal end portion is a cross-sectional view taken along a line Y8A-Y8A in FIG. 8C.
Figure 8B:
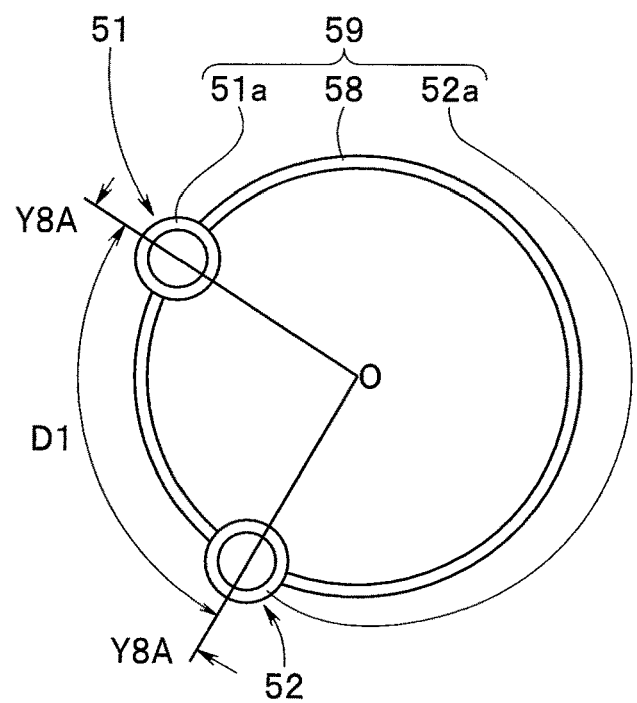
FIG. 8B is a view showing the detachable channel tube as viewed from the distal end surface side.

As shown in FIGS. 8A and 8B, the cap portion 59 includes a tubular cap body 58, and two tube engaging portions 51a and 52a, for example. Each of the tube engaging portions 51a and 52a is provided integrally with the cap body 58 and is a part of each of the channel tubes 51 and 52. The cap body 58 has a predetermined elastic force and is formed to have a predetermined width and wall thickness, thereby being elastically deformable. An inner diameter of a cap of the cap body 58 is set to a predetermined size.

Each of the tube engaging portions 51a and 52a is provided integrally with the cap body 58, is a part of each of the channel tube portions 51 and 52, and is an end portion in the present embodiment. The tube engaging portions 51a and 52a are provided apart from each other. An engaging portion distance between the first tube engaging portion 51a and the second tube engaging portion 52a is set to D1.

The tube engaging portions 51a and 52a may be provided in the middle of parts of the channel tube portions 51 and 52. As a result, the tube distal end surfaces of the channel tube portions 51 and 52 protrude from the distal end surface 20.

Figure 8C:
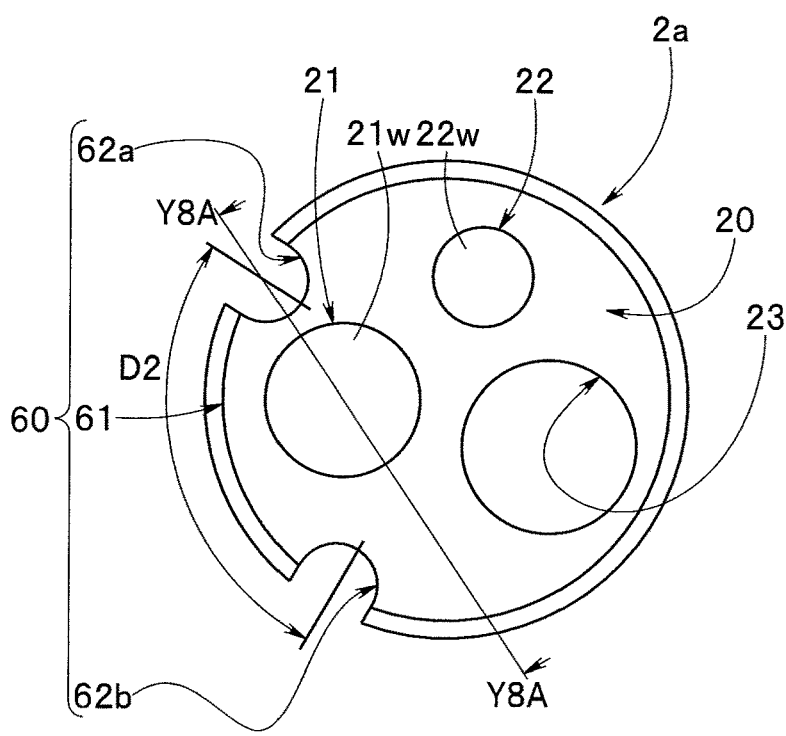
FIG. 8C is a view showing the distal end portion as viewed from the distal end surface side.

As shown in FIG. 8C, a cap mounting portion 60 is provided at the distal end portion 2a. The cap mounting portion 60 includes a cap body mounting portion 61 and tube disposing portions 62a and 62b. The tube engaging portions are disposed in the tube disposing portions. For this reason, the number of tube disposing portions to be provided is equal to the number of tube engaging portions.

The tube disposing portions 62a and 62b has substantially the same shape as the channel fixing portion 24 described above, and are concave grooves provided along the longitudinal axis a2 of the insertion portion 2. Further, other components of the distal end portion 2a are the same as the components in the embodiment described above, and the same members are denoted by the same reference numerals and will not be described.

Figure 8D:
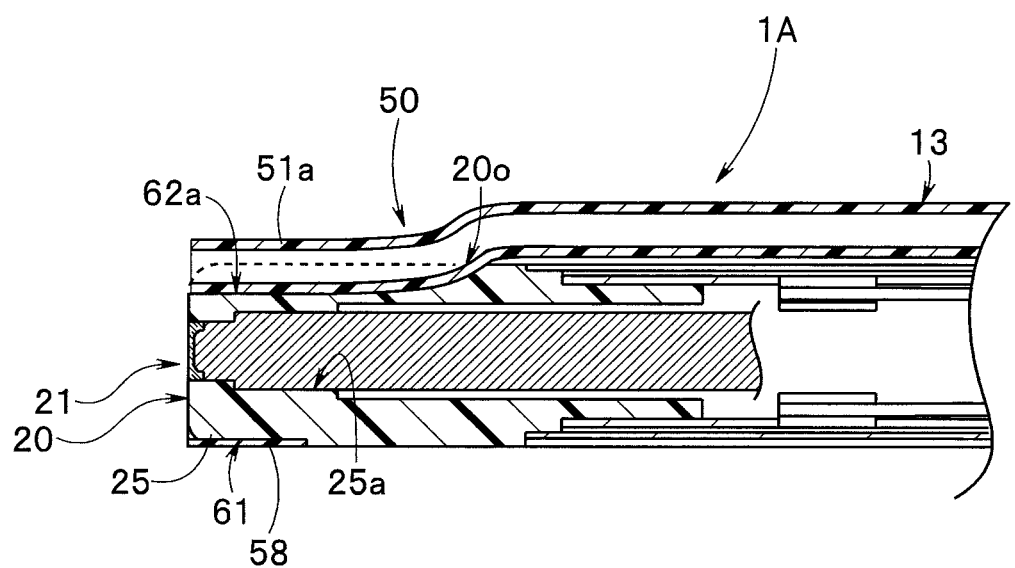
FIG. 8D is a view showing the distal end portion of the insertion portion where the detachable channel tube is disposed.

As shown in FIGS. 8C and 8D, a cap body 58 of the cap portion 59 is disposed in the cap body mounting portion 61. The cap body mounting portion 61 is a circumferential outer peripheral surface provided on the distal end surface 20 side of the distal end portion 2a and is a mounting surface.

The mounting surface of the cap body mounting portion 61 is a stepped surface having a smaller diameter than the distal-end-portion outer peripheral surface 20o by a thickness of the cap body 58. An outer diameter of the mounting surface of the cap body mounting portion 61 is set to a predetermined size.

Then, in a mounted state where an inner peripheral surface of the cap body 58 is disposed on the mounting surface of the cap body mounting portion 61 as shown in FIG. 8D, the cap body 58 has substantially the same outer peripheral surface as the distal-end-portion outer peripheral surface 20o.

On the other hand, the first tube engaging portion 51a is disposed in the first tube disposing portion 62a in an embedded state. The second tube engaging portion 52a is disposed in the second tube disposing portion 62b in an embedded state.

As shown in FIG. 8C, a separation distance between the first tube disposing portion 62a and the second tube disposing portion 62b is set to D2. The distance D1 between the engaging portions is set to be shorter than the separation distance D2 between the disposing portions in advance.

Accordingly, in a state where the first tube engaging portion 51a is embedded in the first tube disposing portion 62a and the second tube engaging portion 52a is embedded in the second tube disposing portion 62b, a force is generated between the first tube engaging portion 51a and the second tube engaging portion 52a to reduce the widened distance D1 between the engaging portions.

In the present embodiment, an inner diameter of the cap of the cap body 58 is set to be smaller than the outer diameter of the mounting surface of the cap body mounting portion 61 by a predetermined size.

Here, the mounting of the detachable channel tube 50 to the distal end portion 2a will be described.

A medical professional attaches the detachable channel tube 50 to the cap mounting portion 60 of the distal end portion 2a to configure an endoscope. First, as shown by an arrow Y8A in FIG. 8A, the medical professional brings the cap body 58 of the cap portion 59 of the detachable channel tube 50 to be closer to the distal end portion 2a.

Next, the medical professional expands the cap body 58 against the elastic force to dispose the cap body 58 on the cap body mounting portion 61, brings the first tube engaging portion 51a to be closer to the first tube disposing portion 62a, and brings the second tube engaging portion 52a to be closer to the second tube disposing portion 62b.

Subsequently, the medical professional embeds the first tube engaging portion 51a in the first tube disposing portion 62a and embeds the second tube engaging portion 52a in the second tube disposing portion 62b, thereby disposing the cap body 58 in the cap body mounting portion 61.

As a result, as shown in FIG. 8D, the detachable channel tube 50 is disposed on the cap body mounting portion 61 and the tube disposing portions 62a and 62b of the cap mounting portion 60 of the distal end portion 2a, thereby the endoscope equipped with the channel tube is configured.

At this time, the inner peripheral surface of the cap body 58 is disposed in close contact with the mounting surface of the cap body mounting portion 61 by the elastic force. In addition, due to a force that is generated between the first tube engaging portion 51a and the second tube engaging portion 52a and tends to reduce the distance D1 between the engaging portions, the first tube engaging portion 51a comes into close contact with the first tube disposing portion 62a, and the second tube engaging portion 52a comes into close contact with the second tube disposing portion 62b, thereby a fixing force increases.

In this way, the detachable channel tube 50 including the cap portion 59 and the plurality of channel tube portions 51 and 52 is configured. On the other hand, the distal end portion 2a of the insertion portion 2 is provided with the cap mounting portion 60 including the cap body mounting portion 61 and the plurality of tube disposing portions 62a and 62b.

According to such a configuration, the cap body 58 of the cap portion 59 is disposed on the cap body mounting portion 61, and the tube engaging portions 51a and 52a of the plurality of channel tube portions 51 and 52 are embedded in the plurality of tube disposing portions 62a and 62b, respectively.

Thus, the elastic force of the cap body 58 and the force generated between the first tube engaging portion 51a and the second tube engaging portion 52a to reduce the distance D1 between the engaging portions serve as a fixing force, and the detachable channel tube 50 is attached to the cap mounting portion 60 by the elastic force, thereby the endoscope equipped with the channel tube can be configured.

The detachable channel tube 50 is removed from the cap mounting portion 60 and discarded after use of the endoscope. Other operational effects are the same as the effects in the embodiment described above.

In the embodiment described above, the number of channel tube portions of the detachable channel tube 50 is two. However, the number of channel tube portions is not limited to two, and may be one or two or more. In addition, the position to be disposed is also set as appropriate.

In the detachable channel tube 50, even when the channel tube portion and the cap body may be integrally formed, or the cap body and the channel tube portion may be separate members, and the two members may be integrally fixed by adhesion or welding.

In the embodiment described above, the inner diameter of the cap of the cap body 58 is set to be smaller than the outer diameter of the mounting surface of the cap body mounting portion 61 by a predetermined size. Further, the separation distance D2 between the disposing portions is set to be larger than the distance D1 between the engaging portions in advance. However, an inner peripheral length of the cap of the cap body 58 may be set to be shorter than the outer peripheral length of the mounting surface of the cap body mounting portion 61.

According to such a configuration, an inner hole of the cap body 58 is not limited to a circular shape. In other words, as long as the inner peripheral length of the cap satisfies the condition described above, the shape of the inner hole of the cap body 58 may be a circular shape or other shapes, such as an ellipse or a polygon, other than the circular shape.

In the embodiment described above, the channel tubes 10, 10A, 10B, 10C, 10D, 10F, 10G, 10H, and 10J disposed to be movable along the outer periphery of the insertion portion 2 and the channel port provided on the tube proximal end side portion 13 of the channel tube portions 51 and 52 are attached and fixed at desired positions of the operation portion 3.

According to the present invention, it is possible to realize an endoscope including the insertion portion in which the channel tubes are disposed on the outer peripheral side of the insertion portion to realize an excellent insertion property, and an endoscope system.

The present invention is not limited to the embodiment described above, and various modifications can be made without departing from the gist of the invention.

What is claimed is:

1. An endoscope comprising:
   an insertion portion configured to be inserted into a subject, the insertion portion comprising a groove recessed relative to an outer circumferential surface of the insertion portion;
   wherein the groove having an inclination surface at least at a proximal end of the groove;
   the inclination surface being inclined in a longitudinal direction of the insertion portion such that the proximal end of the inclination surface terminates at the outer circumferential surface; and
   the groove having a distal portion configured to fix at least a portion of a cross-sectional shape of a channel tube.

2. The endoscope according to claim 1, wherein the inclination surface inclines such that a center axis of the channel tube approaches closer to a longitudinal axis of the insertion portion at a distal end of the groove than at the proximal end of the groove.

3. The endoscope according to claim 2, further comprising:
   an image pickup optical system provided in the insertion portion to observe the subject,
   wherein the groove is configured such that the center axis of the channel tube is inclined with respect to an optical axis of the image pickup optical system.

4. The endoscope according to claim 1, wherein the groove comprises a plurality of grooves and a distal end portion of the insertion portion is provided with the plurality of grooves spaced apart from each other in a circumferential direction.

5. The endoscope according to claim 1, wherein the groove is configured to receive at least a portion of the cross-sectional shape of the channel tube over a predetermined longitudinal length of the insertion portion.

6. The endoscope according to claim 1, wherein the inclination surface is linear in the longitudinal direction of the insertion portion.

7. The endoscope according to claim 1, wherein the cross-sectional shape of the groove in a direction orthogonal to the longitudinal direction is circular to accept the channel tube having a circular cross-section.

8. An endoscope system comprising:
   an endoscope comprising:
     an insertion portion configured to be inserted into a subject the insertion portion comprising a groove recessed relative to an outer circumferential surface of the insertion portion;
     wherein the groove having an inclination surface at least at a proximal end of the groove; and
     the inclination surface being inclined in a longitudinal direction of the insertion portion such that the proximal end of the inclination surface terminates at the outer circumferential surface; and
   a channel tube fixed at least at a distal portion of the groove.

9. The endoscope system according to claim 8, wherein:
   the groove comprises a plurality of grooves provided at a distal end portion of the insertion portion, the plurality of grooves being spaced apart from each other in a circumferential direction; and
   the channel tube comprises a plurality of channel tubes respectively provided in the plurality of grooves.

10. The endoscope system according to claim 9, wherein tube distal end surfaces of each of the plurality of channel tubes respectively disposed in the plurality of grooves are disposed at different longitudinal positions relative to a distal end surface of the insertion portion.

11. The endoscope system according to claim 8, wherein the groove is configured such that the center axis of the channel tube extends towards the longitudinal axis of the insertion portion.

12. The endoscope system according to claim 8, wherein a distal end portion of the channel tube includes a tube inclination surface having a tapered outer shape.

13. The endoscope system according to claim 8, wherein the inclination surface inclines such that a center axis of the channel tube approaches closer to a longitudinal axis of the insertion portion at a distal end of the groove than at the proximal end of the groove.

14. The endoscope according to claim 13, wherein:
   the endoscope further comprising an image pickup optical system provided in the insertion portion to observe the subject,
   wherein the groove is configured such that the center axis of the channel tube is inclined with respect to an optical axis of the image pickup optical system.

15. The endoscope system according to claim 8, wherein the groove is configured to receive at least a portion of the cross-sectional shape of the channel tube over a predetermined longitudinal length of the insertion portion.

16. The endoscope system according to claim 8, wherein the inclination surface is one of curved or linear in the plane in the longitudinal direction of the insertion portion.

17. The endoscope system according to claim 8, wherein the cross-sectional shape of the groove in a direction orthogonal to the longitudinal direction is circular to accept the channel tube having a circular cross-section.

18. An endoscope system comprising:
   an endoscope comprising an insertion portion configured to be inserted into a subject, the insertion portion comprising a plurality of grooves each recessed relative to an outer circumferential surface of the insertion portion; and
   a detachable channel tube comprising:
     a cap body having a tubular shape, the cap body being detachably disposed on the outer circumferential surface of a distal end portion of the insertion portion, and
     a plurality of channel tubes extending from the cap body;
   wherein at least a portion of a cross-sectional shape of a distal end portion of each channel tube is disposed in a respective groove of the plurality of grooves; and
   a circumferential distance between adjacent tubes of the plurality of tubes is shorter than a circumferential distance between corresponding adjacent grooves of the plurality of grooves.

19. The endoscope system according to claim 18, wherein the cap body is elastically deformable, and the cap body is disposed in close contact with the outer circumferential surface of the distal end portion of the insertion portion due to an elastic force of the cap body.

20. The endoscope system according to claim 19, wherein the outer circumferential surface of the distal end portion of the insertion portion, on which the cap body is disposed, has a smaller diameter than an adjacent portion of the outer circumferential surface proximal to the distal end portion by a thickness of the cap body.

\* \* \* \* \*